US009036153B1

(12) United States Patent
Gupta et al.

(10) Patent No.: US 9,036,153 B1
(45) Date of Patent: May 19, 2015

(54) INSTRUMENT FOR REFLECTIVITY MEASUREMENT

(71) Applicant: Google Inc., Mountain View, CA (US)

(72) Inventors: Anurag Gupta, Los Gatos, CA (US); Amber M. Luttmann, Fremont, CA (US); Michael R. Sears, Ben Lomond, CA (US); Evan M. Richards, Santa Clara, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/015,569

(22) Filed: Aug. 30, 2013

(51) Int. Cl.
*G01N 21/55* (2014.01)
*G01N 21/00* (2006.01)

(52) U.S. Cl.
CPC ...................................... *G01N 21/55* (2013.01)

(58) Field of Classification Search
USPC .................................. 356/445–448, 450–458
See application file for complete search history.

(56) References Cited

U.S. PATENT DOCUMENTS

| 3,591,287 | A | | 7/1971 | Hannis |
| 3,951,609 | A | * | 4/1976 | Palenscar .......................... 422/64 |
| 4,123,173 | A | * | 10/1978 | Bullock et al. ................ 356/246 |
| 4,277,177 | A | * | 7/1981 | Larsen et al. ................. 356/431 |
| 4,747,687 | A | | 5/1988 | Hoppe et al. |
| 5,228,462 | A | * | 7/1993 | Osmalov et al. .............. 131/280 |
| 5,314,825 | A | * | 5/1994 | Weyrauch et al. .............. 436/43 |
| 5,546,179 | A | * | 8/1996 | Cheng ............................ 356/73 |
| 5,892,577 | A | * | 4/1999 | Gordon ........................... 356/73 |
| 6,078,443 | A | * | 6/2000 | Yu ................................. 359/892 |
| 6,239,871 | B1 | | 5/2001 | Gilby |
| 6,483,590 | B1 | * | 11/2002 | Davis ............................ 356/445 |
| 6,646,678 | B1 | * | 11/2003 | Kobayashi ................. 348/207.1 |
| 6,927,852 | B2 | | 8/2005 | Reel |
| 7,177,023 | B2 | | 2/2007 | Reel et al. |
| 7,538,878 | B2 | | 5/2009 | Jung et al. |
| 8,054,453 | B2 | | 11/2011 | Harrison |
| 8,299,416 | B2 | | 10/2012 | Arbore et al. |
| 8,591,836 | B2 | * | 11/2013 | Boege et al. .................. 422/552 |
| 2005/0037484 | A1 | * | 2/2005 | Staimer et al. ............. 435/287.2 |
| 2011/0188030 | A1 | * | 8/2011 | Verschuren et al. .......... 356/128 |
| 2012/0088486 | A1 | | 4/2012 | Messerchmidt |

OTHER PUBLICATIONS

Richards, E.M. et al., "Method, Apparatus and System for Transmittance Measurement", U.S. Appl. No. 14/181,083, filed Feb. 14, 2014, Whole Document.

\* cited by examiner

*Primary Examiner* — Kara E Geisel
*Assistant Examiner* — Jarreas C Underwood
(74) *Attorney, Agent, or Firm* — Blakely Sokoloff Taylor & Zafman LLP

(57) ABSTRACT

An apparatus for testing the reflectivity of a material under test includes a rotating carriage, a light source, and a light detector. At least two sample units are mountable to the rotating carriage. Each sample unit includes a planar surface disposed under a portion of a hemispherical surface. The light source is mounted on a pivoting boom and generates light. The light detector is mounted to measure optical power of the light emitted from the light source and reflected from a selected one of the at least two sample units. The pivoting boom and the rotating carriage rotate through different angular positions to obtain reflectance signatures as a function of incident angles for the at least two sample units.

20 Claims, 7 Drawing Sheets

INSTRUMENT FOR REFLECTIVITY MEASUREMENT

TECHNICAL FIELD

This disclosure relates generally to instruments for measuring optical properties of materials.

BACKGROUND INFORMATION

Reflectivity is a measurement of the fraction of incident light (electromagnetic power) that is reflected at an interface between two materials. Reflectivity is a positive real number and equal to the square of the reflection coefficient (a complex number), which measures the fraction of the electric field reflected. The reflectivity of a material layer can vary with both incident angle and wavelength of the light incident on a material layer. Thus, to fully characterize the reflectivity of a material layer for a specific wavelength, reflectivity measurements should be taken at a variety of different incident angles. Fully and accurately characterizing the reflectivity of a material layer can be a time consuming process.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of a system, apparatus, and method of operation for measuring reflectance signature as a function of incident angle in an automated manner are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

It can be relatively straightforward to measure the reflectively of a material layer on a front surface of a planar substrate for all possible angles of incidence. However, this is not the cases when the material layer is disposed below or embedded within a substrate having an index of refraction greater than air. FIG. 1A illustrates such a scenario where a material layer 105 is disposed below a substrate 110 having an index of refraction greater than air. As illustrated, Snell's Law does not allow the internal angle A1 to exceed the critical angle given by $\sin^{-1}(1/n)$, where n is the index of refraction for the material of substrate 110. Thus, even though the external angle of incidence A2 at the top surface of substrate 110 is a grazing angle or near 90 degrees from normal, the internal angle of incidence A1 at the buried material layer 105 is substantially less and limited by Snell's Law.

Figure 1B:
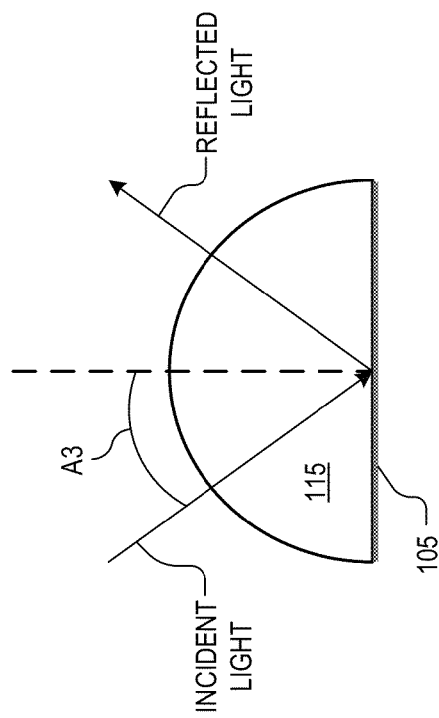
FIGS. 1A & 1B illustrate the issues associated with measuring the reflectivity of a material deposited below a surface.
Figure 1A:
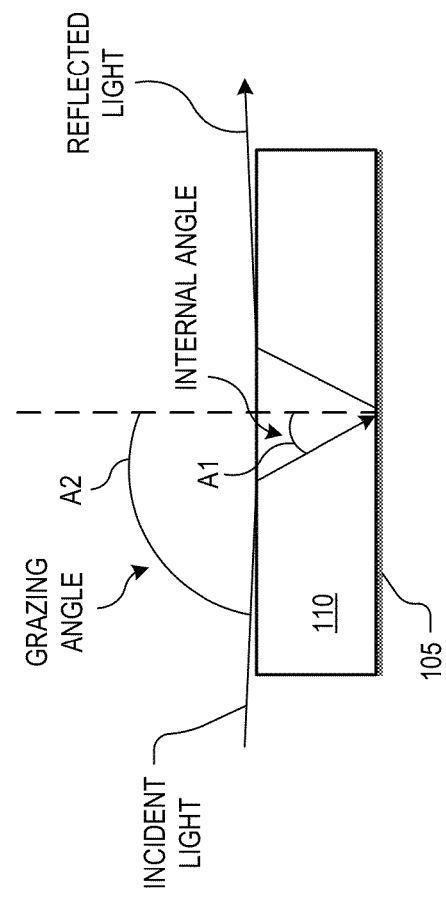

Referring to FIG. 1B, the limitations imposed by Snell's Law can be overcome by disposing material layer 105 below a portion of a hemisphere 115. Hemisphere 115 can be made of the same material as substrate 110 having an index of refraction greater than air. However, if the angle of incidence A3 at the top surface of hemisphere 115 is constrained to always be normal to the surface of hemisphere 115, then the angle of incidence of the light at the surface of material layer 105 will match the angle of incidence A3 and can be tested for all angles 0 through 90 degrees. Embodiments describe herein leverage this technique in an automated system for measuring reflectance signatures as a function of incident angle.

Figure 2A:
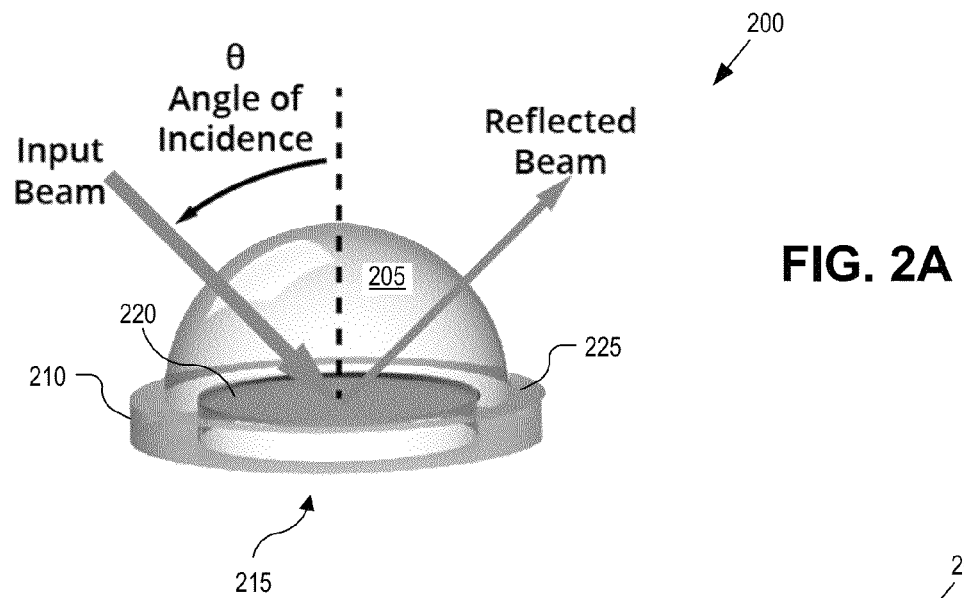
FIGS. 2A-2C illustrate different views and perspectives of a sample unit having a planar surface below a portion of a hemispherical surface for measuring the reflectivity of a material layer, in accordance with an embodiment of the disclosure.
Figure 2B:
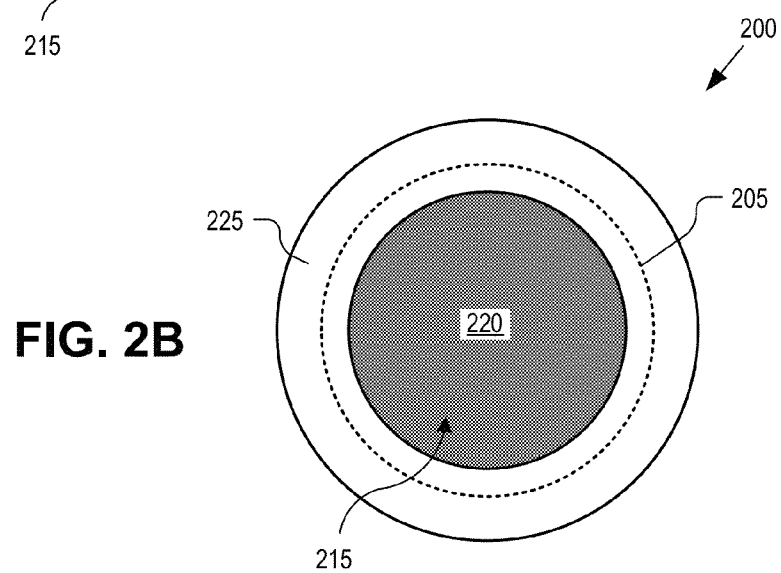
Figure 2C:
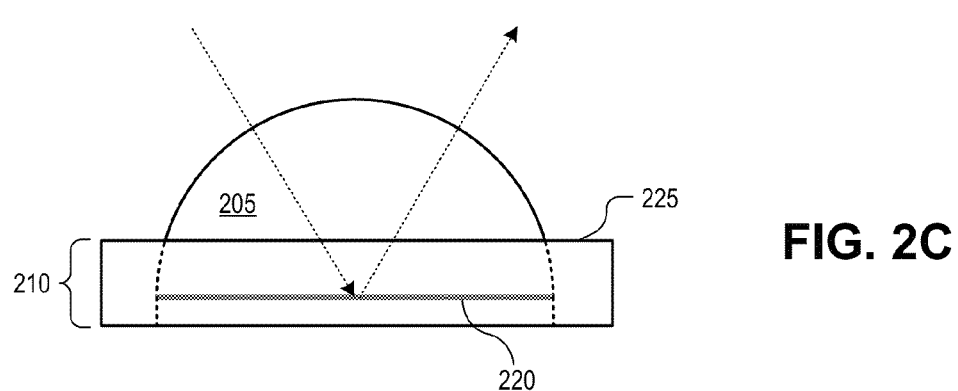

FIGS. 2A-2C illustrate different views and perspectives of a sample unit 200 for measuring the reflectivity of a material layer as a function of angle, in accordance with an embodiment of the disclosure. FIG. 2A is a perspective view of sample unit 200, FIG. 2B is a bottom view of sample unit 200, and FIG. 2C is a cross-sectional view of a slightly modified version of sample unit 200.

The illustrated embodiment of sample unit 200 includes a portion of a hemisphere 205 disposed over a planar substrate 210. The illustrated embodiment of the planar substrate 210 includes recess 215 disposed in its underside which exposes a planar surface upon which a material layer 220 under test is coated. In the illustrated embodiment, planar substrate 210 extends past hemisphere 205 to create a circular flange 225, which may be used for mounting (or otherwise securing) sample unit 200 into an automated system for measuring a reflectance signature of material layer 220.

FIG. 2C illustrates how hemisphere 205 need not be a complete hemisphere, but rather can be implemented with less than a full portion of a hemisphere. However, in this case, the planar surface upon which material layer 220 is coated is offset, such that the planar surface is located at a position that includes a point where all rays normal to the top surface of hemisphere 205 intersect.

The portion of hemisphere 205 and planar substrate 210 maybe formed of a single contiguous block of material or planar substrate 210 may be bonded to the portion of hemisphere 205. Sample unit 200 may be fabricated of plastic (e.g., PMMA, Zeonex™ E48R, etc.), glass, or other optically transmissive materials.

Figure 3:
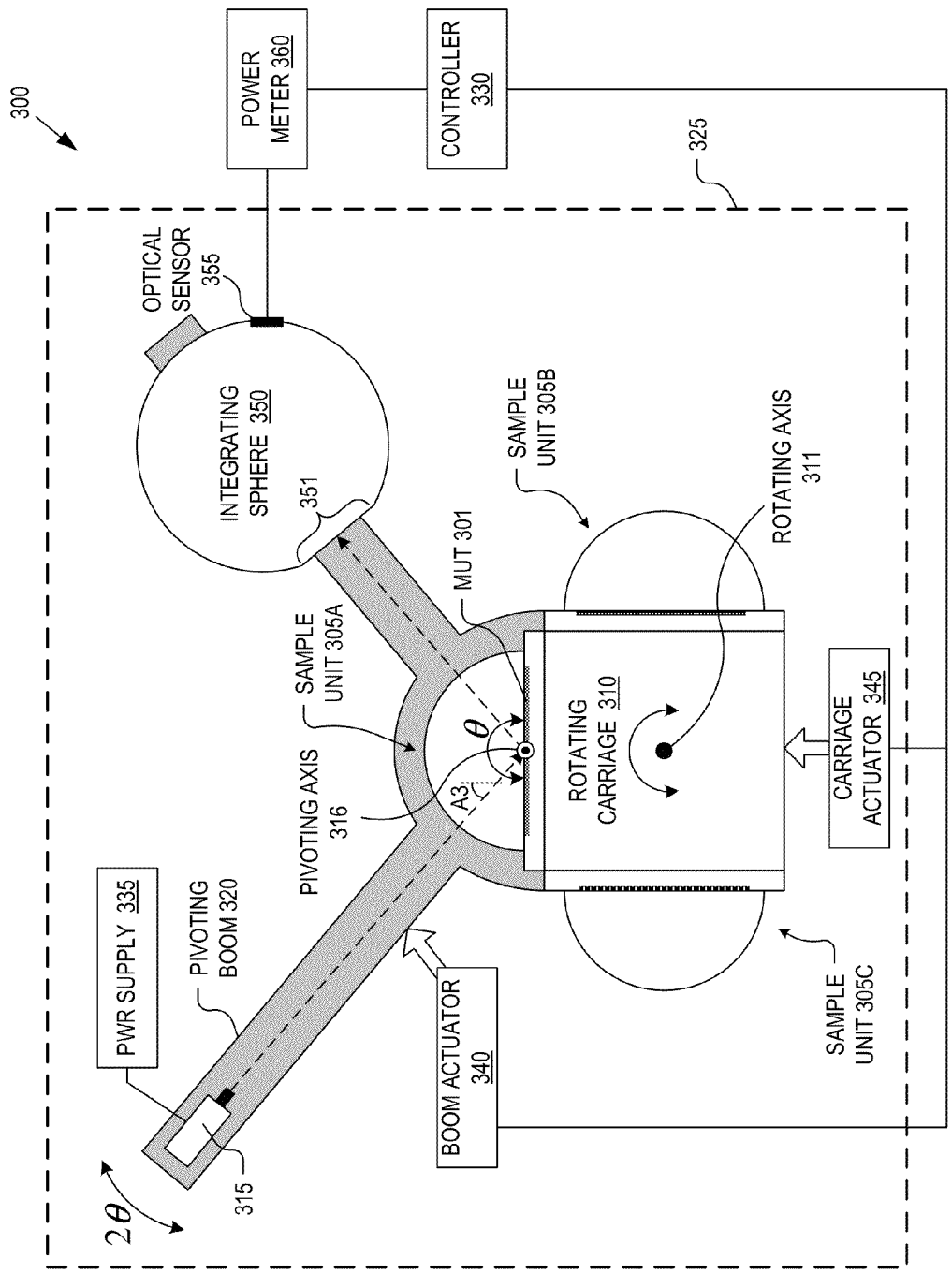
FIG. 3 is a functional block diagram illustrating an automated system for measuring reflectance signatures as a function of incident angle, in accordance with an embodiment of the disclosure.

FIG. 3 is a functional block diagram illustrating an automated system 300 for measuring reflectance signatures as a function of incident angle, in accordance with an embodiment of the disclosure. The illustrated embodiment of system 300 includes sample units 305A, B, and C, a rotating carriage 310, a light source 315, a pivoting boom 320, a light detector, a cover 325, a controller 330, power supply 335, a boom actuator 340, and a carriage actuator 345. The illustrated embodiment of the light detector includes an integrating sphere 350 having an input aperture 351, an optical sensor 355, and a power meter 360.

System 300 operates to measure the reflectivity of a material under test ("MUT") 301 as a function of incident angle A3 in an automated manner. System 300 is capable of supporting multiple sample units 305 (e.g., three are illustrated but anywhere from one to four may be mounted on rotating carriage 310). In typical operation, one sample unit (e.g., sample unit 305A) may contain the MUT 301, while the other sample units 305B and 305C contain reference material layers. System 300 can thus be operated to obtain reflectance signatures from the device under test ("DUT") sample unit and one or more reference sample units, and the deviation of the DUT reflectance signature from the reference reflectance signature(s) characterized. Sample units 305 may be easily mounted on rotating carriage 310 for quick changes; however, it is anticipated that one or two reference sample units 305 may be semi-permanently retained on rotating carriage 310 while the DUT sample unit is swapped out on a regular basis.

For example, one reference sample unit may have hemisphere portion fabricated of plastic while the other reference sample unit may have a hemisphere portion fabricated of glass or other common materials. Furthermore, the material layers disposed under the hemispheres of the reference sample units will typically be made of a material having known or well characterized reflectance signatures and thus suitable for use as a comparative reference for MUT 301 on the DUT sample unit 305A. In one embodiment, the material layer of one of the reference sample units is a simple specular surface (e.g., minor). The reference samples may also be left bare, with no coating, using only total internal reflection ("TIR") to create the reference signature.

Figure 4:
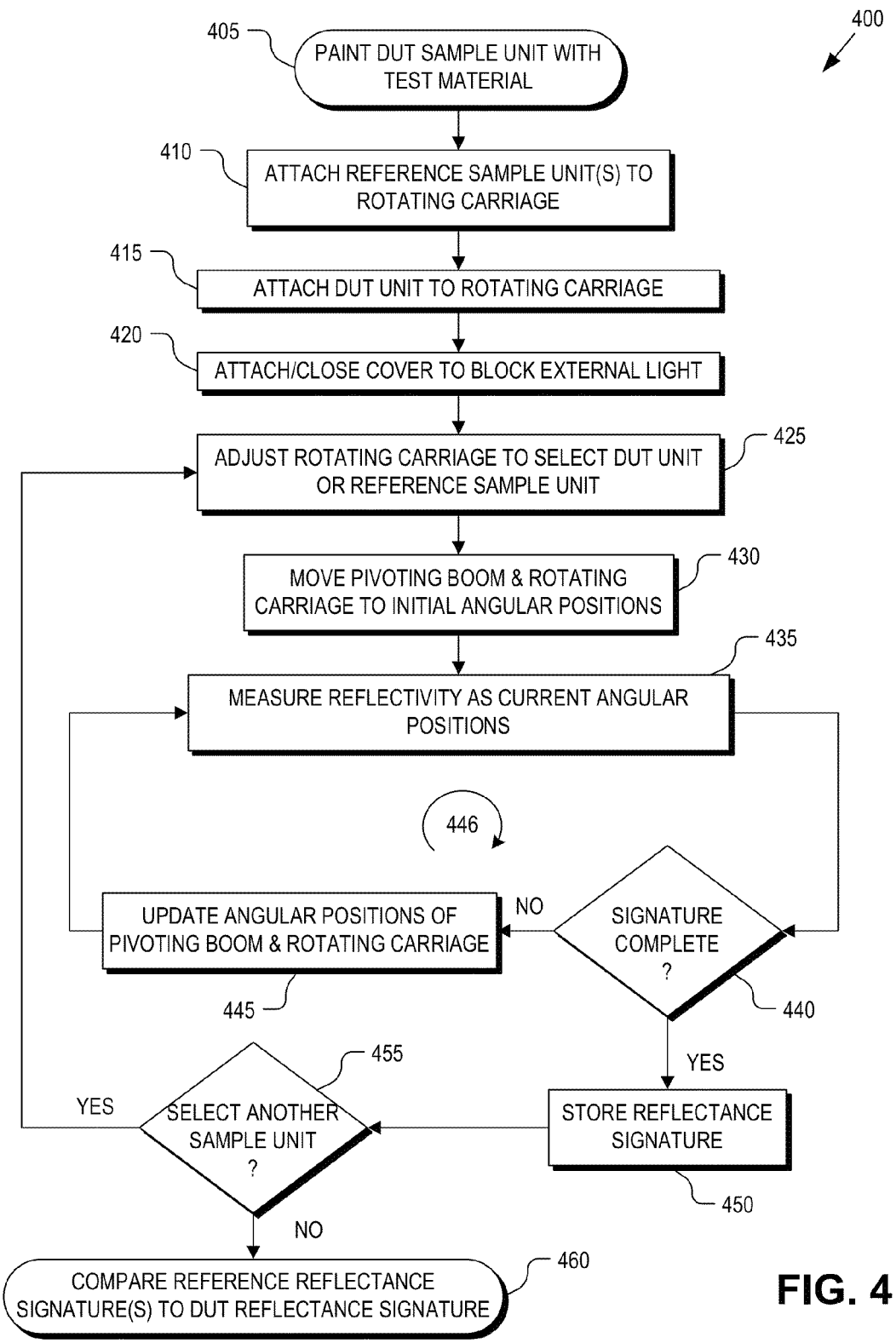
FIG. 4 is a flow chart illustrating a process for measuring a reflectance signature for a material under test, in accordance with an embodiment of the disclosure.

FIG. 4 is a flow chart illustrating a process 400 for measuring a reflectance signature for a material under test ("MUT"), in accordance with an embodiment of the disclosure. Process 400 describes the use and operation of automated system 300 illustrated in FIG. 3. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, the DUT sample unit (e.g., sample unit 305A) is prepared by coating the MUT onto the planar surface within recess 215 on the underside of the DUT sample unit. If the reference sample units (e.g., sample units 305B and/or 305C) are not already mounted to rotating carriage 310, then in a process block 410 they are attached. Similarly, in a process block 415, the prepared DUT sample unit is also attached to a side surface of rotating carriage 310. Sample units 305 may be attached to rotating carriage 310 using a variety of mechanisms including mechanical clasps (e.g., see FIG. 6), temporary glue, pressure fit, threaded attachment, or otherwise.

Figure 7:
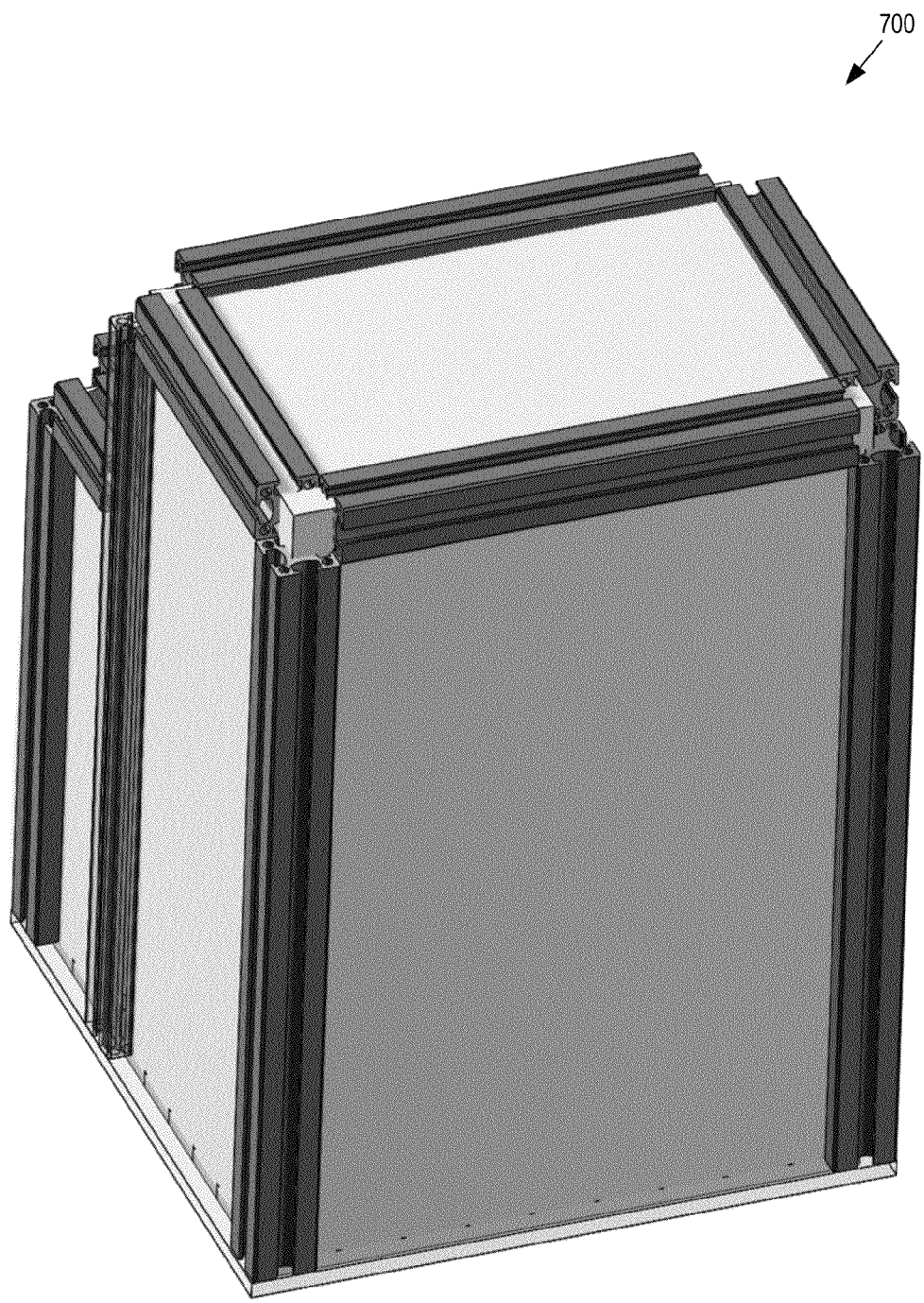
FIG. 7 is a perspective view of a cover for blocking external light, in accordance with an embodiment of the disclosure.

Once all sample units 305 have been attached to rotating carriage 310, cover 325 is placed over system 300, or otherwise closed (processing block 420). Cover 325 is made of an opaque material (e.g., metal or plastic) and blocks external light from interfering with the test measurements. FIG. 7 illustrates an example implementation of cover 325. In one embodiment, a sensor is integrated with cover 325 and senses whether or not the cover is closed to prevent or reduce the incident of operator error contaminating test results with ambient light. Such a sensor may be implemented as a mechanical pressure switch, an electromagnetic contact switch, an optical sensor, or otherwise.

In a process block 425, rotating carriage 310 is rotated to select either one of the reference sample units or the DUT sample unit for testing. As rotating carriage 310 rotates about rotating axis 311, the planar surfaces of sample units 305 are sequentially positioned to be coplanar with pivoting axis 316 of pivoting boom 320. The selected sample unit is the sample unit that is positioned to reflect light emitted from light source 315 to input aperture 351 of integrating sphere 350. Although FIG. 3 illustrates rotating carriage 310 as being a cube having a four sides to which up to four sample unit may be mounted, in other embodiments, rotating carriage 310 may be implemented with other shapes capable of holding more or less sample units (e.g., triangular cross-sectional shape, pentagon cross-sectional shape, etc.).

When a given sample unit (e.g., sample unit 305A) is selected, its planar surface upon which MUT 301 is disposed is coplanar with a pivoting axis 316 about which pivoting boom 320 rotates. In a process block 430, pivoting boom 320 and rotating carriage 310 rotate to their initial or default positions. For pivoting boom 320, the initial/default position may be near vertical (close to normal relative to the plane of MUT 301) or a near grazing angle (close to 90 degrees relative to a normal of the plane of MUT 301). For a selected sample unit 305, rotating carriage 310 also rotates to a default or initial position about a pivoting axis 316. This initial/default angular position of rotating carriage 310 can be different for each selected sample unit, but positions the planar surface having the selected material under test in a complementary position to the initial/default position of pivoting boom 320 such that the light emitted from light source 315 is reflected to input aperture 351. Thus, rotating carriage 310 rotates about rotating axis 311 to select a given sample unit 305 and also rotates sequentially about pivoting axis 316 during testing of a given sample unit 305 to ensure the reflected light beam is directed into aperture 351 of integrating sphere 350.

In a process block 435, the reflectivity of the selected MUT 301 is measured at the current angular positions for pivoting boom 320 and rotating carriage 310. Measuring the reflectivity includes emitting a pulse or continuous emission of light from light source 315 onto MUT 301 through the hemispherical portion of the selected sample unit 305 and measuring the power received at optical sensor 355. In one embodiment, light source 315 is implemented as a laser source (e.g., laser diode) and optical sensor 355 is implemented as a charged coupled device ("CCD") or CMOS image sensor. Of course other light sources and optical sensor technologies may be used.

To account for surface or material imperfections that scatter light, integrating sphere 350 is used to capture and uniformly scatter the reflected light that enters through input aperture 351 regardless of the entrance angle. Thus, the intensity of the reflected light is uniformly distributed over the internal surface of integrating sphere 350. In one embodiment, the light intensity incident upon the finite surface size of optical sensor 355 may be captured for a fixed duration of time generating a power reading by power meter 360. As such, the signal output by optical sensor 355 and the measurement calculated by power meter 360 is indicative of the intensity of the light entering integrating sphere 350, which is in turn related to or indicative of the reflectivity of MUT 301 at the current angular position. The reflectivity reading and the current angular positions (or incident angle A3) is recorded by controller 330 into memory. In one embodiment, controller 330 is implemented as a microprocessor and non-volatile memory storing executable instructions.

If the current reflectance signature associated with the selected sample unit 305 is not yet complete (i.e., more incident angles A3 to test), then process 400 continues to a process block 445. In process block 445, boom actuator 340 and carriage actuator 345 manipulate the current angular positions of pivoting boom 320 and rotating carriage 310, respectively, under the influence of controller 330 to select the next incident angle A3. In order to ensure that the reflect light beam continues to be directed into input aperture 351, in the illustrated embodiment, each angular increment or step of pivoting boom 320 is twice (2θ) each angular increment (θ) of rotating carriage 310 as rotated about pivoting axis 316. Thus, controller 330 causes boom actuator 340 and carriage actuator 345 to sweep through the series of angular positions in a sequential and automated manner.

Boom actuator 340 and carriage actuator 345 may be implemented with a variety of actuating technologies, such as a stepper motor, a servo, or otherwise. In one embodiment, the initial or default positions are identified using a trigger mechanism including optical sensor element(s) positioned to face laser diode element(s). One element is mounted on a fixed position structure of system 300 while the other element is mounted on the moving component (e.g., pivoting boom 320 or rotating carriage 310). When the two elements are aligned, the trigger mechanism is activated indicating a default position is achieved. Other angular feedback mechanisms may also be used such as a rotary encoder.

Loop 446 of process 400 continues until reflectivity measurements have been obtained and recorded for all incident angles A3 of a complete reflectance signature. In one embodiment, a complete reflectance signature may include 80 to 90 measurements obtaining in one degree increments for A3. Other increment sizes and number of discrete measurements may define a complete reflectance signature.

Once a complete reflectance signature for a selected sample unit has been acquired (decision block 440), the reflectance signature has been stored to memory by controller 330 (process block 450), and process 400 continues to a decision block 455. If additional sample units are to be measured, then process 400 loops back to process block 425. For example, the first sample unit measured may contain a reference material layer while the second sample unit measured may contain the material under test. Once all reference reflectance signatures and the DUT reflectance signature have been obtained (decision block 455), the DUT reflectance signature is compared against the one or more reference reflectance signatures. This comparison is performed so that the DUT reflectance signature can be characterized as a deviation or percent deviation from the reference reflectance signatures of know materials.

Figure 5:
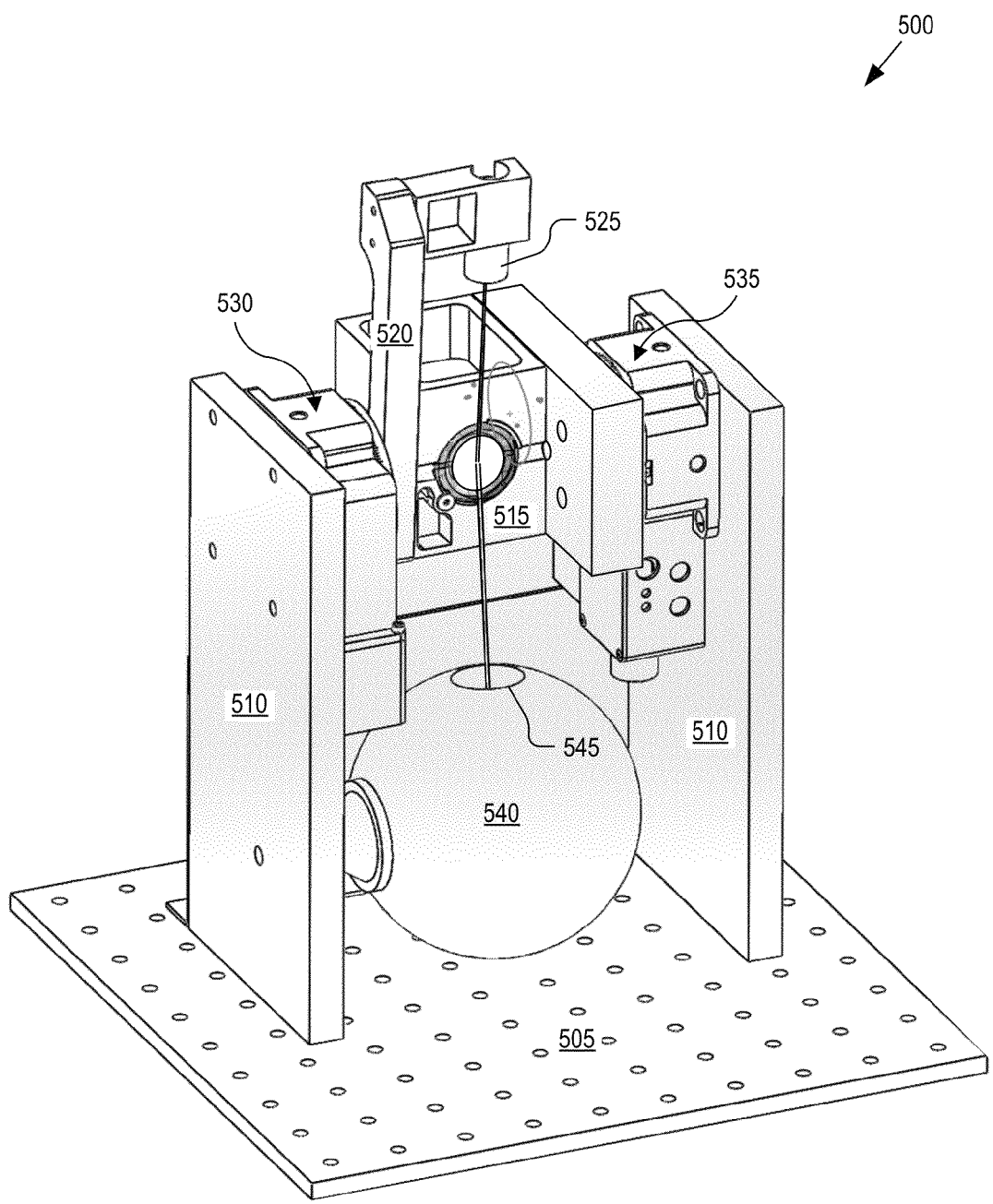
FIG. 5 is a perspective view of an automated system for measuring reflectance signatures as a function of incident angle, in accordance with an embodiment of the disclosure.
Figure 6:
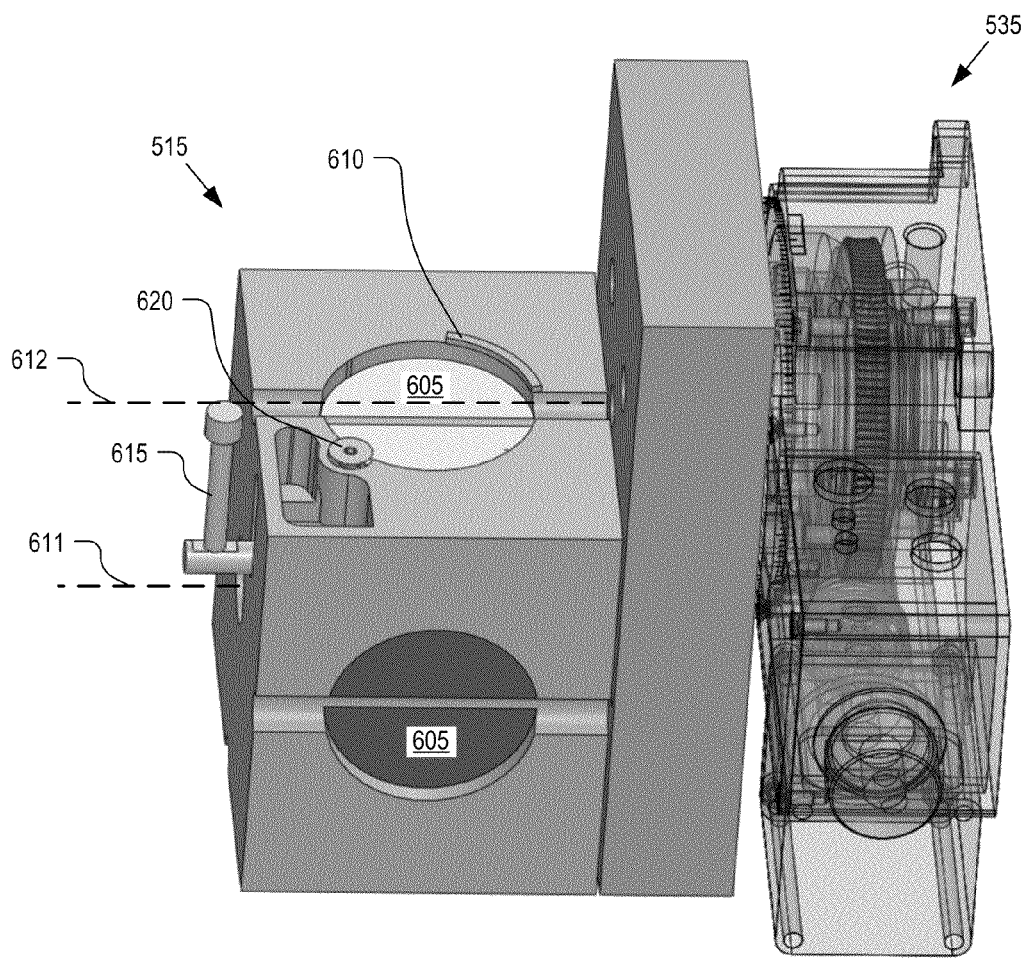
FIG. 6 is a perspective view of a rotating carriage and carriage actuator, in accordance with an embodiment of the disclosure.

FIGS. 5, 6, and 7 illustrate perspective views of different components of an automated reflectance measurement system 500, in accordance with an embodiment of the disclosure. System 500 is one possible implementation of system 300 illustrated in FIG. 3. FIG. 5 is a perspective view of system 500 without its cover. FIG. 6 is a perspective view of a rotating carriage 515 and carriage actuator 535 of system 500. FIG. 7 is a perspective view of a cover 700 of system 500.

Returning to FIG. 5, the illustrated embodiment of system 500 includes the following illustrated components: a base 505, support members 510, a rotating carriage 515, a pivoting boom 520, a laser source 525, a boom actuator 530, a carriage actuator 535, and an integrating sphere 540 with input aperture 545. Of course, system 500 includes the remaining components of system 300, but may not be visible from the illustrated perspective view.

FIG. 6 is an expanded perspective view of rotating carriage 515 and carriage actuator 535 of FIG. 5. The illustrated embodiment of carriage actuator 535 is implemented as a stepper motor as is a known to those skilled in the art of actuating control systems. The illustrated embodiment of rotating carriage 515 includes mounting locations 605 for mounting sample units (e.g., any of sample units 305A, 305B, and 305C) and a locking mechanism for holding sample units at the mounting locations 605. The illustrated embodiment of mounting locations 605 are circular recesses with a ledge 610 that laps over circular flange 225 (see FIGS. 2A-C) to hold the sample unit in place. The illustrated embodiment of the locking mechanism includes a lever 615 that engages a lifting clasp 620 which in connection with ledge 610 holds the sample unit securely in position when engaged.

During operation, rotating carriage 515 rotates about a central rotating axis 611 to select a given sample unit and about a pivoting axis 612 to direct the reflected beam into the aperture of the integrating sphere. In one embodiment, the default location associated with each side of rotating carriage 515 is reached when a non-reflective pattern on the side of rotating carriage 515 is detected by an optical sensor. The angular increments then offset from this default position in a sequential manner in fixed sized increments under the influence of the stepper motor of carriage actuator 535. Of course, in other embodiments, other actuator and feedback sensor mechanisms may be used.

The processes explained above may be described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for testing the reflectivity of a material under test ("MUT"), comprising:
   a rotating carriage configured to receive and to mount one or more sample units, each including a planar surface disposed under a portion of a hemispherical surface;
   a light source to generate light; and
   a light detector mounted to measure optical power of the light emitted from the light source and reflected from a selected one of the one or more sample units,
   wherein the light source and the rotating carriage rotate through different angular positions to obtain reflectance signatures as a function of incident angles for the one or more sample units,
   wherein the light source is mounted to rotate about a pivoting axis that is coplanar with the planar surface of the selected one of the one or more sample units and an optical path of the light emitted by the light source is approximately normal to the hemispherical surface of the selected one of the one or more sample units.

2. The apparatus of claim 1, wherein the selected one of the one or more sample units is selected by rotating the rotating carriage between default locations about a rotation axis that sequentially positions the planar surface of each of the sample units coplanar with the pivoting axis as the rotating carriage is rotated between the default locations.

3. The apparatus of claim 2, wherein the rotating carriage has a square cross-sectional shape with the rotating axis passing through a center of the square cross-sectional shape, wherein the rotating carriage is configured to receive and to mount the one or more sample units along respective sides of the square cross-sectional shape.

4. The apparatus of claim 2, further comprising:
   a pivoting boom to which the light source is mounted;
   a boom actuator mechanically coupled to pivot the pivoting boom about the pivoting axis; and
   a controller coupled to the boom actuator to automatically control the boom actuator to sequentially sweep the pivoting boom through a plurality of boom angular positions.

5. The apparatus of claim 4, further comprising:
   a carriage actuator mechanically coupled to rotate the rotating carriage about the pivoting axis,
   wherein the controller is coupled to the carriage actuator to automatically control the carriage actuator to sequentially sweep the rotating carriage through a plurality of carriage angular positions offset from a selected one of the default locations in synchronicity with the boom angular positions such that the light reflected from the selected one of the one or more sample units reaches the light detector at all boom angular positions.

6. The apparatus of claim 5, wherein boom actuator is configured to increment the boom angular positions in angular steps that are twice the angular size of those of the carriage angular positions.

7. The apparatus of claim 1, wherein the light detector comprises:
   an integrating sphere having a input aperture positioned to receive the light reflected from the selected one of the one or more sample units and to uniformly scatter the light received through the input aperture; and
   an optical sensor disposed on an internal portion of the integrating sphere to capture photons incident upon the optical sensor and coupled to generate a signal indicative of a reflectivity of the a material disposed on the planar surface of the selected one of the sample units.

8. The apparatus of claim 1, wherein the one or more sample units include:
   a first reference unit having the hemispherical surface made of a first material and having a reference material coated on the planar surface; and
   a second reference unit having the hemispherical surface made of a second material different from the first material and having the reference material coated on the planar surface,
   wherein the rotating carriage further includes a third mounting location for accepting a third sample unit as a device under test unit.

9. The apparatus of claim 1, further comprising:
   a cover to block external light; and
   a cover sensor to indicate whether the cover is closed.

10. The apparatus of claim 1, wherein at least one of the sample units comprises:
    a planar substrate over which the portion of the hemispherical surface is disposed;
    a recess disposed in a bottom side of the planar substrate opposite the portion of the hemispherical surface, wherein the planar surface is disposed within the recesses and the MUT is coated on the planar surface,
    wherein the planar substrate extends past the hemispherical surface forming a flange for mounting the sample unit to the rotating carriage.

11. The apparatus of claim 10, wherein the rotating carriage comprises:
    a recess into which the flange of the sample unit is inserted;
    a ledge disposed on a side of the recess to overlap the flange once the sample unit is inserted into the recess; and
    a locking mechanism to hold the sample unit securely in place.

12. A method of measuring a device under test ("DUT") reflectance signature for a material under test, comprising:
    selecting one of multiple sample units mounted to different sides of a rotating carriage by rotating the rotating carriage, wherein each of the sample units includes a planar surface disposed under a portion of a hemispherical surface;
    emitting light from a light source onto the material under test through the hemispherical surface of the selected sample unit;
    obtaining a reflectivity measurement of the material under test with a light detector at current angular positions of the rotating carriage and light source; and
    iteratively repositioning the angular positions of the light source and the rotating carriage to obtain a plurality of the reflectivity measurements to obtain the DUT reflectance signature,
    wherein iteratively repositioning includes rotating the light source about a pivoting axis that is coplanar with the planar surface of the selected one of the sample units,
    wherein an optical path of the light emitted by the light source is approximately normal to the hemispherical surface of the selected one of the sample units.

13. The method of the claim 12, further comprising:
    obtaining a reference reflectance signature from a reference sample unit mounted on the rotating carriage; and
    comparing the DUT reflectance signature to the reference reflectance signature to characterize a reflectance of the material under test as a deviation from the reference sample unit.

14. The method of claim 12, wherein selecting one of multiple sample units comprises:

rotating the rotating carriage between default locations about a rotation axis that sequentially positions the planar surface of each of the sample units coplanar with the pivoting axis as the rotating carriage is rotated between the default locations.

15. The method of claim 14, wherein the rotating carriage has a square cross-sectional shape with the rotating axis passing through a center of the square cross-sectional shape, wherein the two sample units are mounted along respective sides of the square cross-sectional shape.

16. The method of claim 12, wherein rotating the light source about the pivoting axis comprises:
   pivoting a pivoting boom, on which the light source is mounted, with a boom actuator mechanically coupled to pivot the pivoting boom about the pivoting axis; and
   automatically controlling the boom actuator with a controller to sequentially sweep the pivoting boom through a plurality of boom angular positions.

17. The method of claim 16, wherein iteratively repositioning further includes:
   rotating the rotating carriage with a carriage actuator mechanically coupled to rotate the rotating carriage about the pivoting axis; and
   automatically controlling the carriage actuator with the controller to sequentially sweep the rotating carriage through a plurality of carriage angular positions offset from a selected one of the default locations in synchronicity with the boom angular positions such that the light reflected from the selected one of the sample units reaches the light detector at all boom angular positions.

18. The method of claim 17, wherein the boom angular positions are incremented in angular steps that are twice the angular size of those of the carriage angular position increments.

19. An apparatus for testing the reflectivity of a material under test ("MUT"), comprising:
   a rotating carriage to which one or more sample units, each including a planar surface disposed under a portion of a hemispherical surface, are mounted;
   a light source to generate light; and
   a light detector mounted to measure optical power of the light emitted from the light source and reflected from a selected one of the one or more sample units,
   wherein the light source and the rotating carriage rotate through different angular positions to obtain reflectance signatures as a function of incident angles for the one or more sample units,
   wherein the light detector comprises:
      an integrating sphere having a input aperture positioned to receive the light reflected from the selected one of the one or more sample units and to uniformly scatter the light received through the input aperture; and
      an optical sensor disposed on an internal portion of the integrating sphere to capture photons incident upon the optical sensor and coupled to generate a signal indicative of a reflectivity of the a material disposed on the planar surface of the selected one of the one or more sample units.

20. An apparatus for testing the reflectivity of a material under test ("MUT"), comprising:
   a rotating carriage to which at least two sample units, each including a planar surface disposed under a portion of a hemispherical surface, are mounted;
   a light source to generate light; and
   a light detector mounted to measure optical power of the light emitted from the light source and reflected from a selected one of the at least two sample units,
   wherein the light source and the rotating carriage rotate through different angular positions to obtain reflectance signatures as a function of incident angles for the at least two sample units,
   wherein at least one of the sample units comprises:
      a planar substrate over which the portion of the hemispherical surface is disposed;
      a recess disposed in a bottom side of the planar substrate opposite the portion of the hemispherical surface, wherein the planar surface is disposed within the recesses and the MUT is coated on the planar surface,
      wherein the planar substrate extends past the hemispherical surface forming a flange for mounting the sample unit to the rotating carriage.

* * * * *